(12) United States Patent
Govari

(10) Patent No.: US 10,945,781 B2
(45) Date of Patent: Mar. 16, 2021

(54) VARIABLE PHASE GENERATION AND DETECTION FOR RADIO-FREQUENCY (RF) ABLATION

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 311 days.

(21) Appl. No.: 15/697,811

(22) Filed: Sep. 7, 2017

(65) Prior Publication Data

US 2019/0069943 A1 Mar. 7, 2019

(51) Int. Cl.
*A61B 18/12* (2006.01)
*A61B 18/14* (2006.01)
*A61B 18/00* (2006.01)

(52) U.S. Cl.
CPC ...... *A61B 18/1206* (2013.01); *A61B 18/1492* (2013.01); *A61B 2018/0016* (2013.01); *A61B 2018/0075* (2013.01); *A61B 2018/00654* (2013.01); *A61B 2018/00714* (2013.01); *A61B 2018/00732* (2013.01); *A61B 2018/00827* (2013.01); *A61B 2018/00869* (2013.01); *A61B 2018/00892* (2013.01); *A61B 2018/124* (2013.01); *A61B 2018/1273* (2013.01)

(58) Field of Classification Search
CPC ............ A61B 18/1206; A61B 18/1492; A61B 2018/00714; A61B 2018/00732; A61B 2018/0075

See application file for complete search history.

(56) References Cited

U.S. PATENT DOCUMENTS

| 5,383,917 A | 1/1995 | Desai et al. |
| 5,837,001 A | 11/1998 | MacKey |
| 6,050,994 A | 4/2000 | Sherman |
| 6,059,778 A | 5/2000 | Sherman |

(Continued)

FOREIGN PATENT DOCUMENTS

| EP | 2 149 342 A1 | 2/2010 |
| WO | WO 2007/099460 A2 | 9/2007 |
| WO | WO 2013/056266 A2 | 4/2013 |

OTHER PUBLICATIONS

International Search Report dated Jan. 7, 2019, International Application No. PCT/IB2018/056696.

*Primary Examiner* — Michael F Peffley
*Assistant Examiner* — Bo Ouyang

(57) ABSTRACT

A Radio Frequency (RF) ablation system includes a signal generator, control circuitry, a plurality of non-linear amplifiers, and a processor. The signal generator is configured to generate an RF signal having a given frequency. The control circuitry is configured to set phases and amplitudes of a plurality of replicas of the RF signal generated by the signal generator. The plurality of non-linear amplifiers is configured to amplify the plurality of replicas of the RF signal, and to drive a respective plurality of ablation electrodes in a patient body with the amplified replicas. The processor is configured to receive a return signal, including a superposition of the replicas sensed by a patch electrode attached to the patient body, and to adaptively adjust the phases and amplitudes of the replicas in response to the return signal, by controlling the control circuitry.

8 Claims, 3 Drawing Sheets

(56) References Cited

U.S. PATENT DOCUMENTS

| | | |
|---|---|---|
| 6,309,386 B1 | 10/2001 | Bek |
| 6,936,047 B2 | 8/2005 | Nasab et al. |
| 7,252,664 B2 | 8/2007 | Nasab et al. |
| 2003/0199862 A1* | 10/2003 | Simpson ............ A61B 18/1492 606/34 |
| 2004/0044385 A1 | 3/2004 | Fenn et al. |
| 2005/0107834 A1 | 5/2005 | Freeman et al. |
| 2007/0255269 A1 | 11/2007 | Shin |
| 2010/0117659 A1* | 5/2010 | Osadchy ................ A61B 5/053 324/629 |
| 2014/0052126 A1 | 2/2014 | Long et al. |
| 2014/0058248 A1* | 2/2014 | Leussler ............ A61B 18/1815 600/411 |
| 2014/0062593 A1 | 3/2014 | Gilbert |
| 2015/0272655 A1 | 10/2015 | Condie et al. |

\* cited by examiner

VARIABLE PHASE GENERATION AND DETECTION FOR RADIO-FREQUENCY (RF) ABLATION

FIELD OF THE INVENTION

The present invention relates generally to the design of ablation systems, and particularly to the design of multi-electrode cardiac ablation systems.

BACKGROUND OF THE INVENTION

Various known invasive medical instrument designs apply ablative radiofrequency (RF) energy to a patient's tissue using multiple electrodes. For example, U.S. Patent Application Publication 2015/0272655 describes a system and method for preventing unintended tissue damage from the delivery of unintended bipolar RF energy. The system may include a multi-electrode ablation device and an RF delivery unit. The RF delivery unit may transmit unipolar energy to the plurality of electrodes, the energy being in phase, with all electrodes delivering the same voltage and being activated at the same time to deliver no bipolar energy. Additionally or alternatively, the RF delivery unit may transmit bipolar energy to the electrodes. Here, voltage differences between each pair of adjacent electrodes may be monitored and the level of bipolar energy being delivered may be calculated. The voltage of energy delivered to at least one electrode in each adjacent electrode pair may be adjusted if the amount of delivered bipolar energy exceeds a safety threshold.

As another example, U.S. Pat. No. 5,383,917 describes multi-phase RF ablation employing a two-dimensional or three-dimensional electrode array that produces a multitude of current paths on the surface of the ablation zone. This results in a uniform lesion with a size defined by the span of the electrode array. An orthogonal electrode catheter array suitable for cardiac ablation is used in conjunction with a two-phase RF power source to produce uniform square-shaped lesions. Lesions of larger size are created by successive adjacent placement of the square-shaped lesions. A temperature sensor at the electrode tip allows monitoring of ablation temperature and regulation of thereof to minimize the electrode tips from being fouled by coagulum.

U.S. Pat. No. 6,059,778 describes an apparatus for delivering energy to a biological site. The apparatus includes an electrode device having a plurality of electrodes, the electrode device positioned proximal the biological site. A power control system supplies power having a controllable phase angle to each of the electrodes. A backplate is also positioned proximal the biological site so that the biological site is interposed between the electrode device and the backplate. The backplate is maintained at the reference voltage level in relation to the power. The power control system controls the phase angle of the power so that the current flow between the electrodes and between the electrodes and the backplate results in the continuity and depth of lesions desired. In a preferred embodiment, the electrodes are arranged in a substantially linear array.

U.S. Pat. No. 6,050,994 describes an apparatus for delivering energy to a biological site, which includes a catheter having a plurality of electrodes. A power control system supplies power signals, each having a controllable phase angle, to each of the electrodes such that the phase between electrodes alternates. The duty cycle of each electrode is controlled and during the off period of the duty cycle, the phase angles of adjacent electrodes are alternated to achieve a more uniform ablation volume.

U.S. Pat. No. 6,936,047 describes a system for efficient delivery of RF energy to cardiac tissue with an ablation catheter used in catheter ablation, with concepts regarding the interaction between RF energy and biological tissue. Techniques are presented for multichannel simultaneous RF energy delivery with real-time calculation of the probability of coagulum formation. This information is used in a feed-back and control algorithm which reduces the probability of coagulum formation during ablation. For each ablation channel, electrical coupling delivers an RF electrical current through an ablation electrode of the ablation catheter and a temperature sensor is positioned relative to the ablation electrode for measuring the temperature of cardiac tissue in contact with the ablation electrode. A current sensor is provided within each channel circuitry for measuring the current delivered through said electrical coupling and an information processor and RF output controller coupled to said temperature sensor and said current sensor for estimating the likelihood of coagulum formation. When this functionality is propagated simultaneously through multiple ablation channels, the resulting linear or curvilinear lesion is deeper with less gaps.

U.S. Pat. No. 5,837,001 describes a radio-frequency ablation system in which the power, voltage, or temperature delivered to multiple electrodes may be dynamically controlled, and in which the electrodes may be simultaneously energized in phase with each other to achieve a desired lesion pattern. The system comprises a multiple electrode ablation catheter, each electrode having a temperature sensor operatively associated therewith. Each electrode is energized by its own RF amplifier, and all of the electrodes are driven in phase with each other by a common sine wave oscillator. A feedback network controls the degree of amplification of the separate RF amplifiers. According to a further aspect of the invention, a modular power supply arrangement is disclosed which is configurable to dynamically control the power, voltage, or temperature delivered to multiple electrodes of a multipolar ablation device. An arbitrary number of electrodes may be simultaneously energized in phase with each other to achieve a desired lesion pattern using the modular power supply by providing a sufficient number of removable modules.

U.S. Pat. No. 7,252,664 describes system and method for efficient delivery of RF energy. At least a single channel card is removably coupled to a backplane for controlling the amount of RF power delivered through a single channel via an electrical coupling to at least one ablation electrode or a catheter. The at least one channel card provides a gradual increase in RF power calculated in real-time during an initial ramp-up phase, and to limit the delivery of RF power through the electrical coupling based on a received temperature of cardiac tissue in contact with the at least one ablation electrode, thereby reducing the likelihood coagulum formation.

SUMMARY OF THE INVENTION

An embodiment of the present invention that is described herein provides a Radio Frequency (RF) ablation system including a signal generator, control circuitry, a plurality of non-linear amplifiers, and a processor. The signal generator is configured to generate an RF signal having a given frequency. The control circuitry is configured to set phases and amplitudes of a plurality of replicas of the RF signal generated by the signal generator. The plurality of non-linear amplifiers is configured to amplify the plurality of replicas of the RF signal, and to drive a respective plurality of ablation electrodes in a patient body with the amplified replicas. The processor is configured to receive a return signal that includes a superposition of the replicas sensed by a patch electrode attached to the patient body, and to adaptively adjust the phases and amplitudes of the replicas in response to the return signal, by controlling the control circuitry.

In some embodiments, the amplifiers include Class-D amplifiers. In some embodiments, the ablation system includes a plurality of measurement circuits, configured to measure the replicas amplified by the respective plurality of amplifiers, and the processor is configured to adjust the phases and the amplitudes of the replicas based on the measured replicas.

In an embodiment, the control circuitry is configured to adjust one or more of the plurality of amplified replicas within given limits. In some embodiments, the control circuitry is configured to maintain one or more crosstalk currents, which flow through the patient body between the ablation electrodes, within given limits.

There is additionally provided, in accordance with an embodiment of the present invention, a method for Radio Frequency (RF) ablation. The method includes generating an RF signal having a given frequency. A plurality of replicas of the RF signal are amplified, and a plurality of ablation electrodes in a patient body is driven with the amplified replicas, using a respective plurality of non-linear amplifiers. A return signal, which includes a superposition of the replicas sensed by a patch electrode attached to the patient body, is received. The respective phases and amplitudes of the replicas are adaptively adjusted in response to the return signal.

The present invention will be more fully understood from the following detailed description of the embodiments thereof, taken together with the drawings in which:

DETAILED DESCRIPTION OF EMBODIMENTS

Overview

Figure 1:
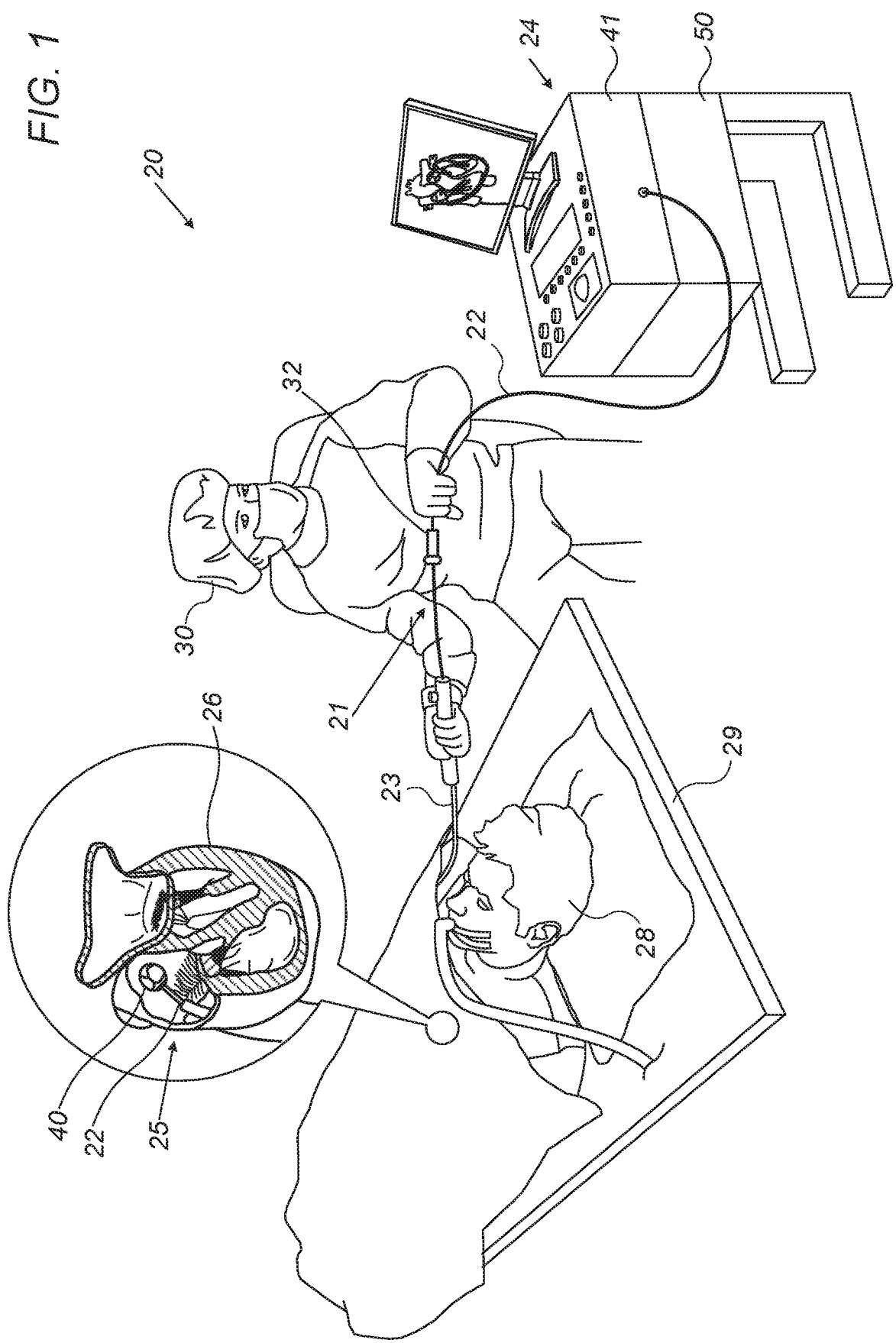
FIG. 1 is a schematic, pictorial illustration of a catheter-based ablation system, in accordance with an embodiment of the present invention.

Embodiments of the present invention that are described herein provide improved methods and systems for RF power delivery and control of multi-electrode RF ablation devices, using a plurality of non-linear amplifiers and phase-shifters, or schemes based on similar principles.

In some embodiments, an RF ablation device comprising a plurality of electrodes is fitted at the distal end of a catheter. Each electrode is fed separately via a respective non-linear amplifier, e.g., a Class-D amplifier. The amplifiers amplify respective replicas of a common signal generated using a common RF generator.

A control unit sets the target amplitude values for the amplifiers. Prior to amplification, the control unit sets the phases of each of the replica signals, in a step named in the description hereafter 'phase-selection' (in the enclosed description 'phase selection' means setting desired relative phase differences between the replicas to be amplified by the amplifiers). A back patch, attached to the patient's skin, acts as the common return electrode for collecting the total return current. In some embodiments, voltage and current measurement circuits measure the amplifiers output voltages and currents.

Analysis circuitry configured to use an optimization algorithm, named collectively hereinafter 'an analyzer,' analyzes the injected currents and return current amplitude and phase information in real-time. The analysis may involve, for example, measuring the instantaneous amplitude and phase of the return current at a very high rate. The analyzer then determines, in real-time, the current amplitudes that are actually injected from each and every one of the electrodes. Based on requirements implemented in the given optimization algorithm, the analyzer calculates new amplitudes and phases for the injected currents that are better optimized to meet the algorithm targets, some of which are detailed below. The analyzer may be implemented using custom-made hardware and software or utilize any commercial available tools to perform the set of tasks described above.

The control unit receives the optimized amplitudes and phases values in real-time, and instructs the phase-shifters and/or amplifiers to modify at least part of the injected currents phases and/or amplitudes.

During the ablation process, the electrode voltages are susceptible to variations due to the real-time changes in the resistance of the tissue along the various individual instantaneous electrical paths involved. This effect causes varying voltage-differences between electrodes, resulting in mostly ill uncontrolled, undesired, varying electrical currents between the electrodes, known as crosstalk currents.

In some embodiments, the disclosed system can force in real-time a certain current waveform of each and every one of the electrodes, throughout the ablation process. In this manner, all the electrodes potentials can be actively kept practically equal during ablation. To achieve this goal, the amplitudes and phases of the waveforms are reselected at sufficient high rates and with short enough response times, according to the system requirements derived from the clinical needs implemented in the algorithm targets, such as for example of keeping the crosstalk currents below certain values, and even practically cancel them altogether in certain cases.

Non-linear amplifiers, such as Class-D amplifiers, use non-linear pulse-modulation techniques to tailor their instantaneous output electrical power, and are known to be highly efficient and agile. Thus, the disclosed technique can readily cope with real-time requirements induced by the clinical needs, such as exemplified above, while still meeting the demand for high electrical peak powers. Other non-linear amplification schemes comprising, for example, other classes of non-linear amplifiers that are suitable for performing the same tasks, may also be used.

The disclosed RF power generation and control system is thus especially beneficial when applying the RF ablative power in a single shot simultaneously through a plurality of electrodes, a mode of operation which requires both tight control of the instantaneous voltage and current of each of the electrode, and an availability of peak electrical power in the range of several kilo-Watts, putting high demands both on the ablation-system and on the electric infrastructure of the treatment-arenas.

The disclosed technique has, for example, a clear power efficiency advantage over legacy solutions that generate RF energy at different frequencies for the different electrodes, since such multi-frequency power generators requires the use of inefficient linear amplifiers, such as for example Class-A amplifiers. Multi-frequency powering and control schemes are also less capable of controlling the adverse crosstalk currents, as compared with the disclosed system and technique capabilities.

Avoiding the crosstalk currents can potentially reduce clinical side-effects, such as for example shallow lesions when deep ones are desired. Avoiding the crosstalk currents may be also beneficial because for example, these may cause electrical instabilities during the ablation process, making the process less efficient and its expected positive impact on the target tissue less predictable.

An additional advantage of the Class-D based ablation system is, for example, the use of a single frequency currents for all the electrodes, which simplifies the generation of the currents and the analysis and control of the individual currents, and can assist in the realization of complicated multi-electrode architectures.

System Description

FIG. 1 is a schematic, pictorial illustration of a catheter-based ablation system 20, in accordance with an embodiment of the present invention. System 20 comprises a catheter 21, wherein a shaft 22 of the catheter is inserted into a heart 26 of a patient 28 through a sheath 23. The proximal end of catheter 21 is connected to a control console 24. In the embodiment described herein, catheter 21 may be used for any suitable therapeutic and/or diagnostic purposes, such as electrical sensing and/or ablation of tissue in heart 26.

Console 24 comprises a processor 41, typically a general-purpose computer, with suitable front end and a control unit 50 for receiving signals from catheter 21, as well as for applying energy via catheter 21 to ablate tissue in heart 26 and for controlling the other components of system 20.

A physician 30 inserts shaft 22 through the vascular system of patient 28 lying on a table 29. Catheter 21 comprises a balloon assembly 40 fitted at the distal end of shaft 22. During the insertion of shaft 22, balloon assembly 40 is maintained in a collapsed configuration. Physician 30 navigates balloon assembly 40 to a target location in heart 26 by manipulating shaft 22 using a manipulator 32 near the proximal end of the catheter. Once the distal end of shaft 22 has reached the target location, physician 30 inflates balloon assembly 40 and operates console 24 so as sense signals and apply ablation energy to the tissue at the target location.

Variable Phase Generation and Detection for RF Ablation

Figure 2:
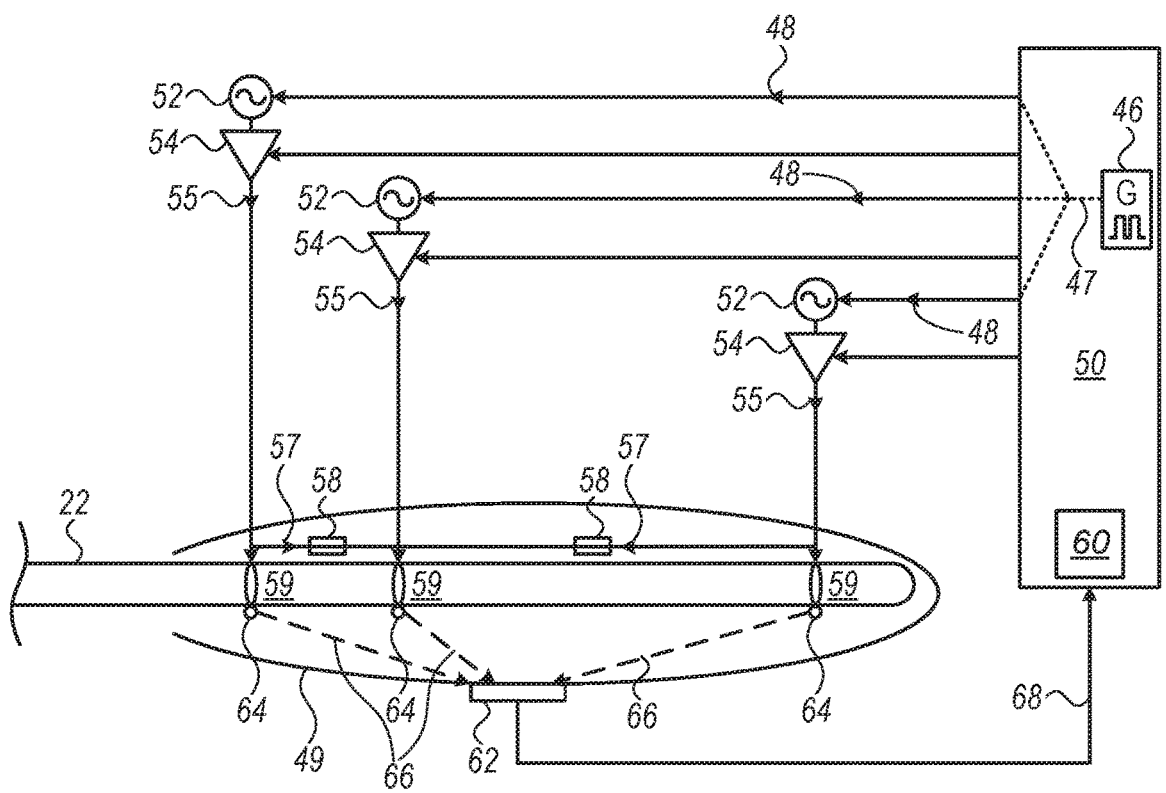
FIG. 2 is a schematic diagram of an ablation system using Class-D amplifiers, in accordance with an embodiment of the present invention.

FIG. 2 is a schematic diagram of catheter-based ablation system 20 using Class-D amplifiers 54, in accordance with an embodiment of the present invention. Physically, as illustrated, a catheter distal end 22 is fitted with an RF ablation device comprising a plurality of electrodes 59, wherein the outputs of amplifiers 54 are each coupled to an electrode 59 by wiring passing through the catheter, which is coupled at its proximal end to control-console 24 comprising control unit 50.

In FIG. 2, the catheter distal end is shown as a linear array of electrodes only for clarity. In practice, the distal end typically comprises a multi-electrode geometry suitable for the ablation procedure in question. Example configurations are an inflatable-balloon or an extendable-basket assembly, used for performing ablation of pulmonary veins.

In the present example, control unit 50 controls in parallel a number of Class-D amplifiers that is equal to the number of electrodes 59. Each of the Class-D amplifiers comprises a phase-shifter 52 and an amplifier 54. Control unit 50 comprises a common signal generator 46 that generates a common RF signal 47, split into replicas 48 of the RF signal 47, for driving amplifiers 54. Control unit 50 commands separately each of phase-shifters 52 to assign a respective phase to an input current waveform of amplifier 54, which is then amplified to become output current waveform 55 injected to a patient's body 49 through the associated electrode 59.

As seen in the figure, resulting ablation-currents 66 flow locally through the ablated tissue 64 and then through the patient body 49 and are collected by a common back patch electrode 62. The finite resistance of tissue between any two each electrode, however, for example through blood in the case of ablation of blood vessels, as illustrated by coupling resistances 58, can cause part of the injected currents 55 to take a path from one electrode to another in the form of crosstalk currents 57.

Control unit 50 comprises an analyzer 60, which analyzes a return current 68 waveform and based on its measured instantaneous amplitude and phase, possibly among other inputs required for the calculation, determines the actual current amplitudes of each of the injected ablation-currents 66. Based on requirements and calculation steps implemented in the given optimization algorithm, the analyzer adjusts the amplitudes and/or phases of one or more of currents 55 to optimize currents 55 amplitudes and phases for meeting certain requirements, some of which are detailed below. Control unit 50 receives these optimized amplitudes and phases in real-time, and instructs phase-shifter 52 and/or amplifiers 54 in real-time to responsively modify at least part of the injected phases and amplitudes of currents waveforms 55. In a possible implementation, a given optimization algorithm may utilize the instantaneously measured output voltages and currents of amplifiers 54 for adjusting in real time crosstalk currents 57. For example, the algorithm may diagonalize a 'current matrix', as to zero crosstalk currents 57. Additionally or alternatively, other optimization algorithms may be applied, utilizing given constrains and/or cost functions, such as those incorporating the measured instantaneous amplitude and phase of back patch electrode 62.

Figure 3:
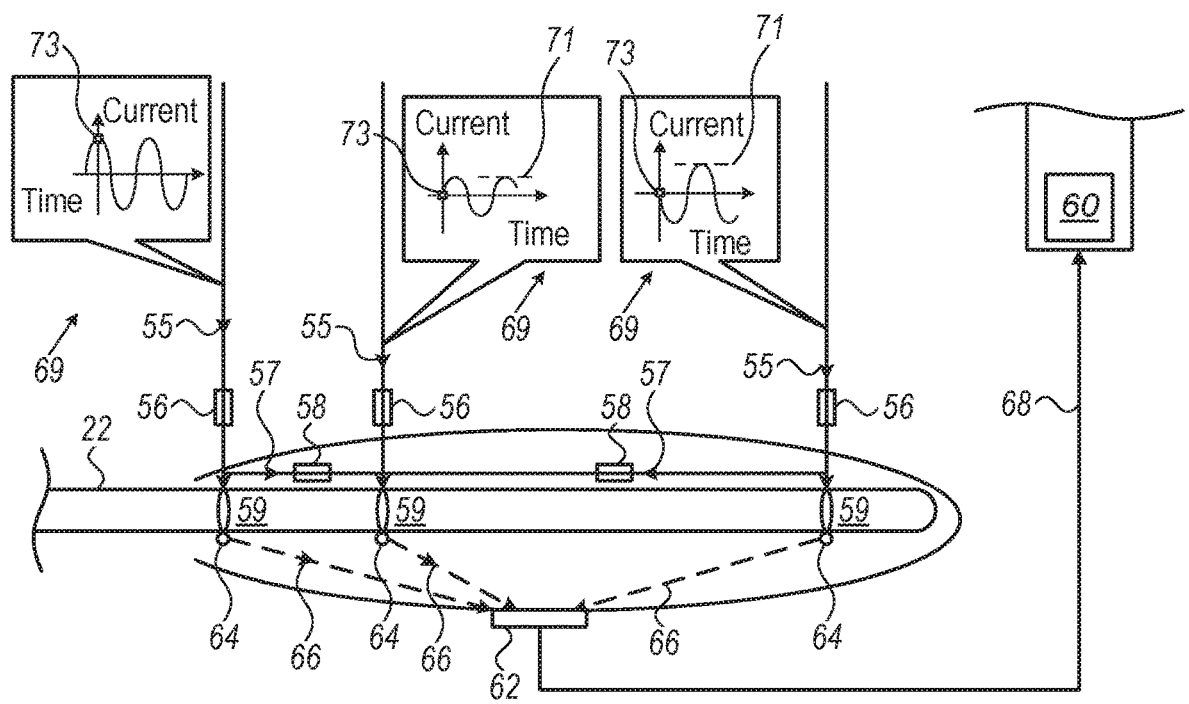
FIG. 3 is a schematic diagram showing certain details of the ablation system operation, in accordance with an embodiment of the present invention.

FIG. 3 is a schematic diagram showing certain details of the ablation system operation, in accordance with an embodiment of the present invention. As seen in the figure, the waveforms in insets 69 comprise in general different values of amplitudes 71 and phases 73. Voltage and current sensors 56 measure the amplifiers output voltage and currents, and analyzer 60 measures the return current 68 instantaneous amplitude and phase and uses this information, among others, for extracting the actual electrode output voltage and currents. The disclosed method thus isolates and measures the various current amplitudes 55 and 66 of each and one of electrodes 59 and deduce the crosstalk currents 57.

crosstalk currents 57 can be reduced and even canceled by forcing similar, or practically identical, voltages on part or all of the electrodes 59 in real-time during the ablation process. This setting is achieved by modulating the currents of all electrodes with the same frequency □, and by selecting in real-time the individual amplitudes and phases of current waveforms 55, as seen in insets 69. Thus, when the voltage differences between any two electrodes (namely, over resistances 58) are kept minimal at all times, the cross-talk currents between any two electrodes are reduced and even canceled altogether in certain cases.

As noted above, to practically achieve such a minimization of constantly varying crosstalk currents, or even their cancelation, the return current 68 should be analyzed by analyzer 60 at sufficiently high rate such that amplitude and phase selection occur at a sufficiently high rate and with short enough response times. This closed-loop fit of analysis modification of the currents can be achieved by using proper electronic circuits and non-linear amplifiers, such as phase-shifters and Class-D amplifiers operating, for example, at the hundreds MHz frequencies range.

Figure 4:
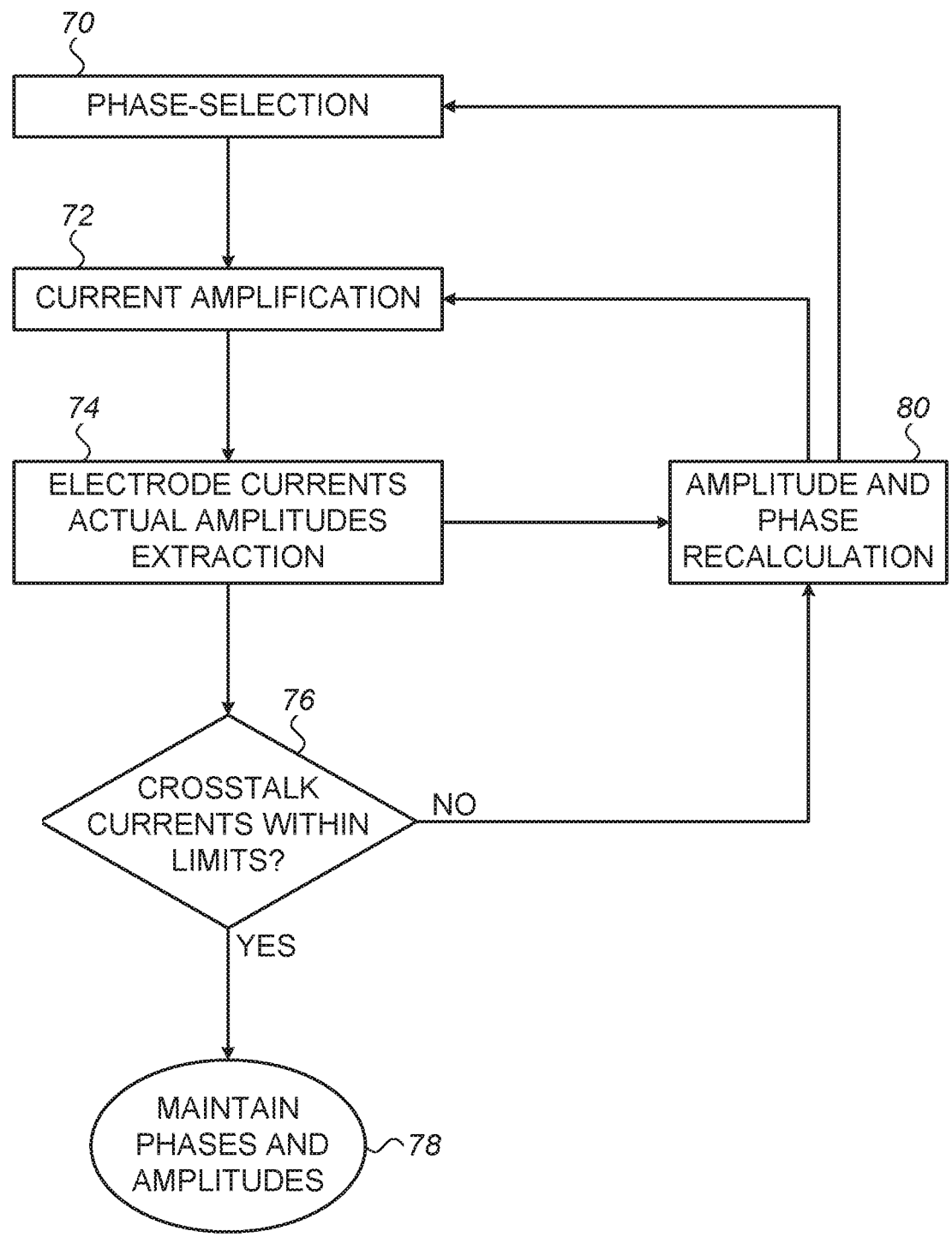
FIG. 4 is a flow chart that schematically illustrates a method for controlling ablation currents, in accordance with an embodiment of the present invention.

FIG. 4 is a flow chart that schematically illustrates a method for controlling ablation currents, in accordance with an embodiment of the present invention. As seen, the crosstalk currents values are controlled in a closed loop. Phase-shifters 52 assign a phase to each of replicas 48 of the RF signal 47, at a phase-selection step 70. Amplifiers 54 set the amplitude of each of the currents 55, at a current amplification step 72.

Back patch 62 collects the actual ablation-currents 66 and analyzer 60 analyzes their amplitudes in real-time, using for the analysis the measured output voltages and currents of amplifiers 54, provided by sensors 56, at an electrode currents actual amplitudes extraction step 74. Knowing currents 55 in real-time enables analyzer 60 to extract the real-time values of crosstalk currents 57. Analyzer 60 compares crosstalk currents 57 values with the specified limits, at a decision step 76. If crosstalk currents are within predefined limits, then no action is taken, and the various amplitudes phases are maintained, as seen at a maintaining phases and amplitudes step 78. If one or more of the crosstalk currents exceed limits, then analyzer 60 recalculates the amplitudes and phases, at an amplitude and phase recalculation step 80. The method loops back to steps 70 and 72 and proceeds, until the ablation process is completed.

The example configurations shown in the figures are chosen purely for the sake of conceptual clarity. In alternative embodiments, the disclosed techniques may use any other suitable amplification schemes and types of amplifiers performing the set of tasks described above, comprising for example amplification circuitry different than such based on Class-D amplifiers.

The various system elements shown in FIGS. 1-3 can be implemented using suitable hardware or firmware. For example, generator 46 can be implemented in a suitable high-speed Field-Programmable Gate Array (FPGA) or Application-Specific Integrated Circuit (ASIC). Certain system elements, such as, for example, analyzer 60, may be implemented using software running on a programmable processor, or using a combination of hardware and software elements.

The optimization targets may relate to any of the output currents and voltages. Furthermore, the ablation device may have different geometries, such as of an inflated balloon, a spiral, a multi-arm and more. The ablation device may comprise temperature sensors in proximity to the electrodes, wherein the system may use an algorithm comprising electrode temperatures for controlling at least part of the ablation process.

Although the embodiments described herein mainly address ablation applications, the methods and systems described herein can also be used in other medical applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A Radio Frequency (RF) ablation system, comprising:
a signal generator disposed in a control unit outside a patient body, the signal generator configured to generate an RF signal having a given frequency;
control circuitry, configured to set phases and amplitudes of a plurality of replicas of the RF signal generated by the signal generator;
a plurality of non-linear amplifiers, configured to amplify the plurality of replicas of the RF signal, and to drive a respective plurality of ablation electrodes in a patient body with the amplified replicas, wherein each of the plurality of non-linear amplifiers is coupled to each of the plurality of ablation electrodes by wiring passing from the control unit outside the patient body to a catheter disposed inside the patient body; and
a processor, configured to receive a return signal, comprising a superposition of the replicas sensed by a patch electrode attached to the patient body, and to adaptively adjust the phases and amplitudes of the replicas in response to the return signal, by controlling the control circuitry, wherein the control circuitry is configured to maintain one or more crosstalk currents, which flow through the patient body between the ablation electrodes, within given limits by comparing the crosstalk currents values with specified limits such that if the crosstalk currents values are within predefined limits, then the amplitudes and phases are maintained else if one or more of the crosstalk currents exceed limits, then the processor recalculates the amplitudes and phases.

2. The ablation system according to claim 1, wherein the amplifiers comprise Class-D amplifiers.

3. The ablation system according to claim 1, and comprising a plurality of measurement circuits, configured to measure the replicas amplified by the respective plurality of amplifiers, wherein the processor is configured to adjust the phases and the amplitudes of the replicas based on the measured replicas.

4. The ablation system according to claim 1, wherein the control circuitry is configured to adjust one or more of the plurality of amplified replicas within given limits.

5. A method for Radio Frequency (RF) ablation, comprising:
generating an RF signal having a given frequency;
amplifying a plurality of replicas of the RF signal, and driving a plurality of ablation electrodes disposed in a patient body with the amplified replicas, using a respective plurality of non-linear amplifiers disposed in a control unit outside the patient body;

receiving a return signal, comprising a superposition of the replicas sensed by a patch electrode attached to the patient body; and adaptively adjusting respective phases and amplitudes of the replicas in response to the return signal, wherein the adaptively adjusting respective phases and amplitudes comprises adjusting one or more crosstalk currents, which flow through the patient body between the ablation electrodes, within given limits by comparing the crosstalk currents values with specified limits such that if the crosstalk currents values are within predefined limits, then the amplitudes and phases are maintained else if one or more of the crosstalk currents exceeds limits, then the processor recalculates the amplitudes and phases.

6. The method according to claim 5, wherein the amplifiers comprise Class-D amplifiers.

7. The method according to claim 5, further comprising measuring the plurality of replicas amplified by the respective plurality of amplifiers, and adjusting the phases and the amplitudes of the replicas based on the measured replicas.

8. The method according to claim 5, wherein the adaptively adjusting respective phases and amplitudes comprises adjusting one or more of the amplified replicas within given limits.

* * * * *